United States Patent [19]

McGeehan et al.

[11] Patent Number: 5,411,858
[45] Date of Patent: May 2, 1995

[54] MANUFACTURING PROCESS FOR SAMPLE INITIATED ASSAY DEVICE

[75] Inventors: John K. McGeehan, Woodbury; Gerhard Ertingshausen, Princeton, both of N.J.; Timothy B. Meluch, Bear, Del.

[73] Assignee: ActiMed Laboratories, Inc., Burlington, N.J.

[21] Appl. No.: 104,934

[22] Filed: Aug. 12, 1993

Related U.S. Application Data

[63] Continuation of Ser. No. 824,252, Jan. 22, 1992, abandoned, which is a continuation-in-part of Ser. No. 749,521, Aug. 26, 1991, Pat. No. 5,234,813, which is a continuation-in-part of Ser. No. 352,985, May 17, 1989, Pat. No. 5,087,556.

[51] Int. Cl.$^6$ ........................................... G01N 33/531
[52] U.S. Cl. ........................................ 435/4; 435/805; 435/970; 436/161; 436/514; 436/518; 436/528; 436/800; 436/805; 436/810
[58] Field of Search ...................................... 422/56–58; 427/2; 435/4, 970, 805; 436/514, 518, 528, 164, 169, 800, 805, 810

[56] References Cited

U.S. PATENT DOCUMENTS

| | | | |
|---|---|---|---|
| 3,690,836 | 9/1972 | Buissiere et al. | 435/34 |
| 3,802,842 | 4/1974 | Lange et al. | 436/86 |
| 3,847,553 | 11/1974 | Verbeck | 435/28 |
| 3,992,158 | 11/1976 | Przybylowicz | 436/170 |
| 4,258,001 | 3/1981 | Pearce et al. | 422/56 |
| 4,312,834 | 1/1982 | Vogel | 422/56 |
| 4,776,904 | 10/1988 | Charlton et al. | 435/805 |
| 4,999,285 | 3/1991 | Stiso | 422/58 |
| 5,087,556 | 2/1992 | Ertingshausen | 436/514 |
| 5,104,811 | 4/1992 | Berger et al. | 422/56 |
| 5,120,643 | 1/1989 | Ching et al. | 422/56 |

FOREIGN PATENT DOCUMENTS

| | | |
|---|---|---|
| 0183442 | 6/1986 | European Pat. Off. . |
| 0271204 | 6/1988 | European Pat. Off. . |
| 0271854 | 6/1988 | European Pat. Off. . |
| 0299428 | 1/1989 | European Pat. Off. . |
| 345460 | 12/1989 | European Pat. Off. . |
| 0408222 | 1/1991 | European Pat. Off. . |
| 0423784 | 4/1991 | European Pat. Off. . |
| 2204398 | 11/1988 | United Kingdom . |

*Primary Examiner*—David Saunders
*Assistant Examiner*—Christopher L. Chin
*Attorney, Agent, or Firm*—Iver P. Cooper

[57] ABSTRACT

A quantitative test device is manufactured using a feedback loop which allows one to modify continuously the dimensions of a reading scale printed on the device. The quantitative test device is manufactured by attaching the critical component of a two-component dye system to minute particles such as microcrystalline cellulose, silica, or latex, which particles are suspended in a solution of a polymeric binder. Additional non-immobilized components of the reaction system of the test device are optionally added to the polymer solution. The suspension of dyed particles in polymer solution is applied to a fabric as a coating, using conventional coating machines, to obtain a homogeneous distribution of immobilized dye throughout the fabric.

The device includes a measurement zone which is made from a film support made of a material having a lower melting point than the filter cloth fabric used in the measurement zone was used. By using a lower melting point material for the support film, impulse heat sealing is controlled to a degree such that the lower melting point support is made to melt and extrude through the mesh of the fabric on either side of a channel, forming a seal along the sides of the channel.

10 Claims, 3 Drawing Sheets

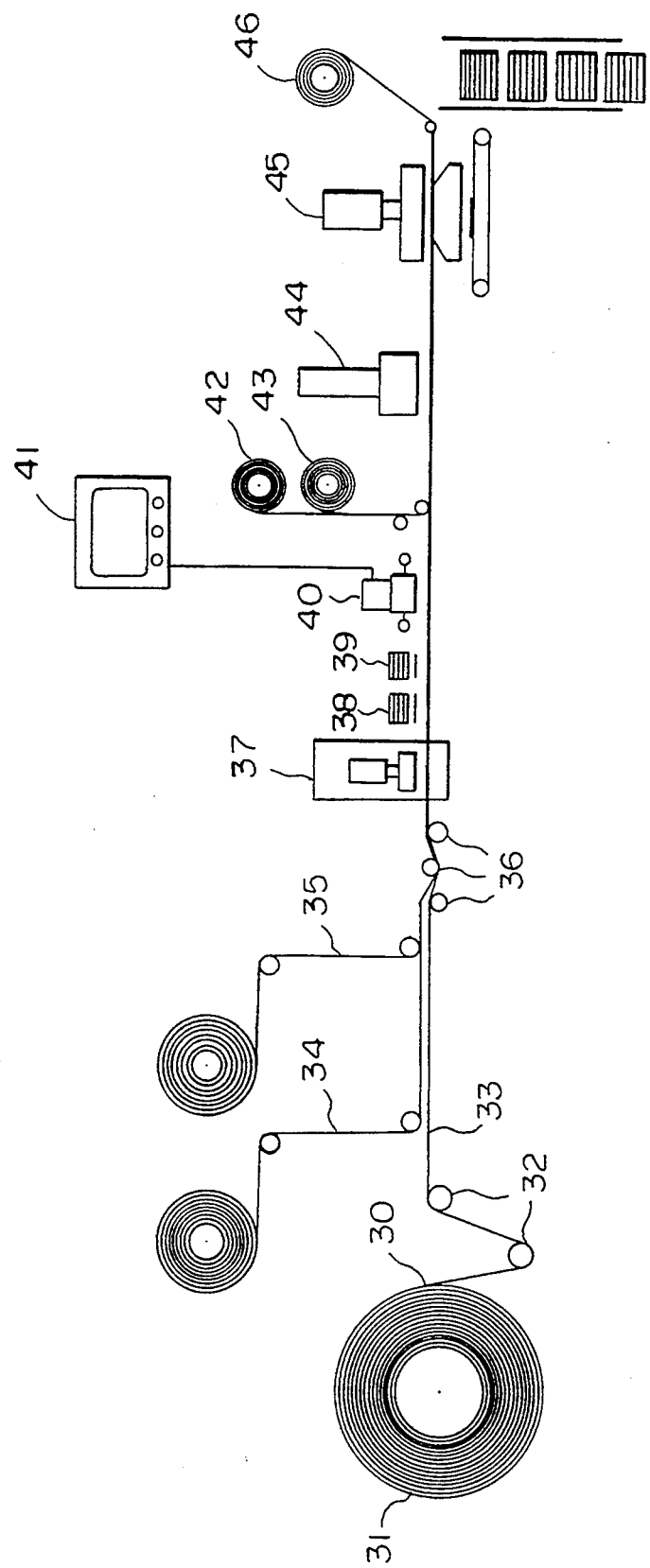
F/G. 2

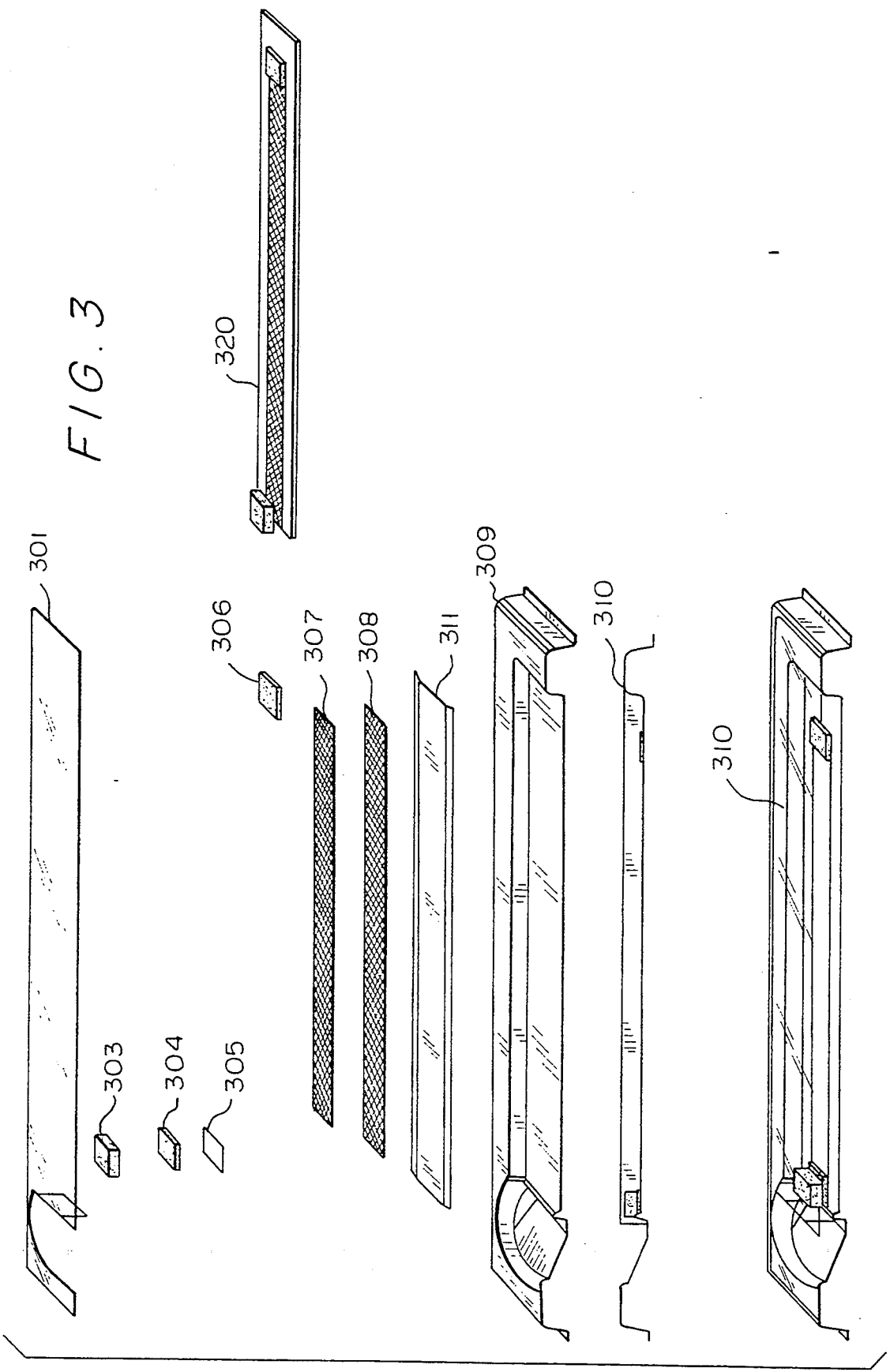

MANUFACTURING PROCESS FOR SAMPLE INITIATED ASSAY DEVICE

This application is a continuation of application Ser. No. 07/824,252, filed Jan. 22, 1992, now abandoned, which is continuation-in-part of application Ser. No. 07/749,521, filed Aug. 26, 1991, now U.S. Pat. No. 5,234,813, which is a continuation-in-part of application Ser. No. 07/352,985, filed May 17, 1989, now U.S. Pat. No. 5,087,556, which are incorporated herein in their entirety by reference.

FIELD OF THE INVENTION

The present invention is directed to a method for manufacturing a quantitative test device. More specifically, the present invention is directed to a method for manufacturing a device for quantitatively analyzing the constituents of whole blood or other body fluids with self-contained, ready-to-use test strips.

BACKGROUND OF THE INVENTION

Medical science has an increasing need for quick, accurate determination of analytes in blood or other body fluids. Traditionally, assays for analytes have been performed by laboratories and required skilled technicians, complex apparatus and reagents, and considerable time in order to obtain accurate results. A great number of qualitative and some quantitative devices and methods have been developed which eliminate or decrease the need for laboratory diagnostic services. Many of these devices and methods include test strips or dip sticks which can be exposed to blood or another body fluid in order to obtain a diagnostic result. A common example of this technology includes the various test products for determining glucose concentration for diabetics to monitor their glucose levels.

Flow devices for quantitative analytical measurements are currently available. However, their utility has been significantly hampered by materials and processes for producing the devices which are unsuitable for use with fully automated and internally controlled manufacturing. The need for such automation and process control is particularly important for the reliability of devices which do not rely on comparative measurements involving the use of single or multiple calibration standards prior to running the test sample in the final analysis.

Among the problems encountered in manufacturing these flow devices are the problems of trapping the indicator in such a manner that a reliable, accurate determination can be made. A number of prior art workers have described such assay devices, but heretofore there has not been a method that can be automated for making a reliable quantitative device.

Previous methods for preparing flow devices for quantitative measurements involve immobilizing an indicator dye on an absorbant support, typically a special paper in roll or sheet form, where the immobilization process involves chemical reactions which are difficult to control, and washing steps. It is very difficult to achieve uniform distribution of immobilized dye molecules throughout the sheets or from beginning to end of a roll of this paper. Additionally, the mechanical effects of processing can degrade the physical integrity of a paper and result in variable wicking and volume of fluid uptake. The variations in the chemical and physical behavior of sheets prepared in this manner are significant, and adversely affect the precision of assays conducted with these devices.

Przybylowicz, in U.S. Pat. No. 3,993,158, discloses an integral element for analyses of liquids which comprises an isotropically porous spreading layer which contains microparticles trapped in a thin film of hydrophilic polymer such as polyvinyl alcohol or gelatin. The only purpose of this layer is to spread liquid quickly so that even flow of liquid occurs into and through the layer to the bottom thereof, where another layer takes up the liquid to subject its components to a specific analytical test. The particles in the spreading layer do not contain any covalently linked chromatic indicators.

Pearce et al., in U.S. Pat. No. 4,258,001, disclose another type of spreading layer containing polymeric, nonporous particles linked with small amounts of adhesive, which provide large open spaces between the beads because the adhesive only connects individual beads without filling the interstitial spaces. This makes for a very effective spreading layer. Any chemical reactants in the layer are adsorbed to the beads and are not covalently bound. Such a layer would not be suitable for use in a flow-through device because reagents such as the dye chromogen would leach out of the spreading layer if subjected to lateral flow of the sample.

Vogel, in U.S. Pat. No. 4,312,834, uses particles in films to make the film porous to larger molecules. Immunoglobulins and albumin are important components of human blood which do not easily diffuse into polymer films containing chemical reactants. When these films are "opened" by the addition of particles such as fumed silica or microcrystalline cellulose, these large molecules are given access to chemical integrated into the film. The particles trapped in the films described by Vogel, however, are not covalently bound to the chemical reactants, and are therefore not suitable for flow devices in which lateral flow may elute reagents and reaction products. This elution precludes the formation of a distinct, sharp front of a color bar needed to derive quantitative visual results.

Pierce et al., in U.S. Pat. No. 4,258,001, disclose an element for the analysis or transport of liquids comprising a plurality of heat-stable, organo-polymeric particles non-swellable in and impermeable to the liquid, and an adhesive concentrated at the particle surface areas contiguous to adjacent particles bonding the particles into a coherent, three-dimensional lattice that is non-swellable in the liquid.

Siegel et al., in European patent No. 345 460 disclose a test device using covalently immobilized colored dyes wherein a second component of a two component dye system is covalently bonded to a matrix. Color is formed when a first component, which may be the analyte or another dye component, covalently couples to the second component. The color formed is covalently immobilized to the matrix.

SUMMARY OF THE INVENTION

It is an object of the present invention to overcome the aforementioned disadvantages. The present invention provides a method for manufacturing a quantitative test device. The test device produced according to the present invention has a flow channel which has a precise volume, and the length of a developed color bar is controlled.

In the method according to the present invention, a quantitative test device is manufactured using a feedback loop which allows one to modify continuously the dimensions of a reading scale printed on the device.

According to the present invention, a method is provided for manufacturing a quantitative test device by attaching the critical component of the dye system to minute particles such as microcrystalline cellulose, silica, or latex. These particles were subsequently suspended in an aqueous or nonaqueous solution of a polymeric binder such as polyvinyl alcohol, polyvinyl acetate, cellulose acetate, or the like. Additional non-immobilized components of the reaction system of the test device can also be added to the polymer solution if desired. The suspension of dyed particles in polymer solution was applied to a fabric as a coating, using conventional coating machines. After drying a homogeneous distribution of immobilized dye throughout the fabric was obtained. This homogeneous distribution of the dye through the fabric was not eluted by the sample's flowing through the measurement zone.

In order to obtain accurate determinations of the component being measured, it is important to control the dimensions, and therefore the volume, of the channel through which the sample flows in the measurement zone of the device. A film support made of a material having a lower melting point than the filter cloth fabric used in the measurement zone was used. By using a lower melting point material for the support film, impulse heat sealing is controlled to a degree such that the lower melting point support is made to melt and extrude through the mesh of the fabric on either side of the channel, forming a seal along the sides of the channel. The sample can then flow through the open mesh of the fabric in the channel defined by the heat seals, and the volume of the channel is defined by the very uniform thickness of the filter cloth and the distance between the seals.

The quantitative device made according to the present invention forms a color bar to indicate the quantity of analyte present in the sample. The length of this color bar is controlled for any given analyte concentration by controlling the application of the non-immobilized component of a two part dye system along the length of the measurement zone. The critical reaction limiting component of the chromatic detection system is applied to the coated fabric in the measurement zone of the device, where the second dye component is immobilized on particles in the coating. The non-immobilized dye component is conveniently and precisely applied, such as with an ink-jet printer, where the amount of solution deposited and the time of deposition is controlled by computer. In this manner, the relationship between the length of the color bar and the analyte concentration can be expressed as a linear or nonlinear function by controlling the concentration gradient of the non-immobilized dye component along the length of the measurement zone.

Because the process of the present invention can be easily automated and form part of a continuous manufacturing line, an additional aspect of the manufacturing process of the present invention can be effected wherein the measurement scale printed along the measurement zone is part of a feedback control system. At intervals during the continuous automated production of the device, sample devices are taken and run using an analyte sample of a known concentration. The lengths of the resultant color bars are continuously compiled and subjected to trend analysis during the production run, and the distances between divisions of the measurement scale are automatically adjusted using the software which controls the operation of the printer. By providing continuous adjustment of the measurement scale, the undesirable effect of signal drift on accuracy due to manufacturing variables is minimized.

BRIEF DESCRIPTION OF THE DRAWINGS

FIG. 2 is a schematic of an inset assembly line according to the present invention.

FIG. 3 is an exploded view of a device produced according to the present invention.

BRIEF DESCRIPTION OF THE INVENTION

Figure 1:
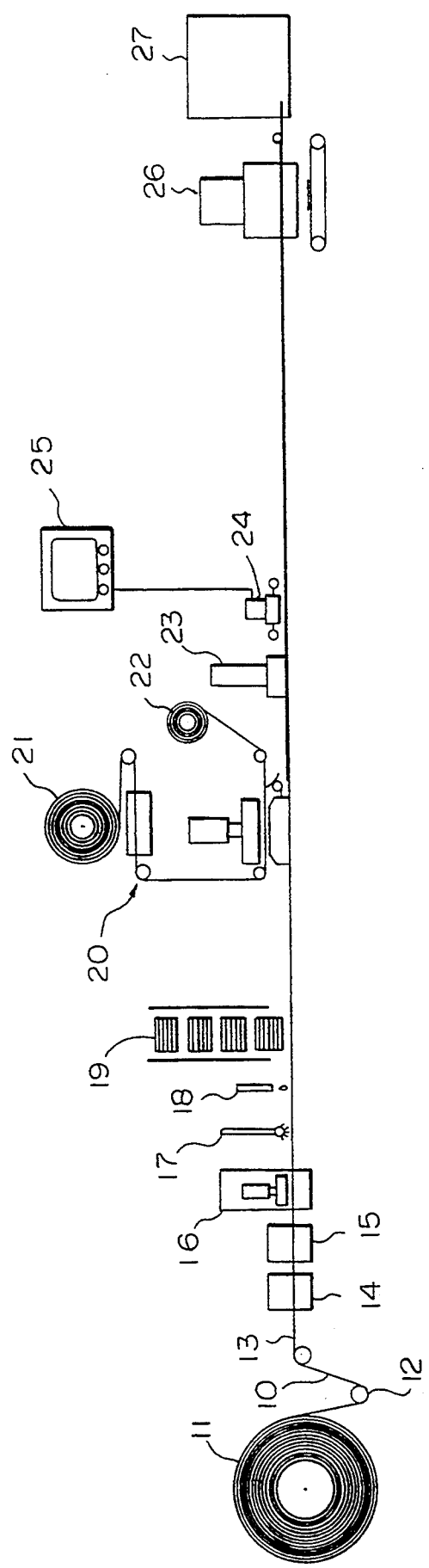
FIG. 1 is a schematic of a main assembly line according to the present invention.

Referring to FIG. 1, film 10 is supplied from a reel 11 through a roller 12 from which the film moves onto a belt 13. The film is first preheated at a preheating station 14, after which the film is heated at a heating station 15. The film is thermoformed into the desired configuration at the thermoform station 16, and then is corona treated by a corona discharge device 17. A surface coat is applied to the treated film by a coating means 18. Channel inserts 19 are then applied to the film. The film is then covered by a cover film 20 from a cover film supply 21. This cover film 20 may be printed with any desired indicia of origin. Excess film is taken up at a waste windup 22. The assembled device is sealed ultrasonically by an ultrasonic sealing device 23. A scale is then printed onto the device by a suitable printer 24. A computer 25 controls the calibration of the printing by taking measurements at predetermined intervals and adjusting the printing mechanism to ensure that the scale printed onto the device is accurate. The individual devices are punched out by a punching means 26, and excess film is transferred to a waste shredder 27.

Inserts for the device, which carry the reactants and the indicators for the analytes, are made on a separate assembly line, shown in FIG. 2. Film support for the insert 30 is drawn off from a film supply 31, passed over rollers 32 onto a conveyor 33, and channel fabric 34 and dye layer fabric 35 are successively laid on top of the support film. The layers pass through tensioning rollers 36 and are then heat sealed together by heat seal means 37. Enzyme dispensers 38 and draw zone dispensers 39 dispense appropriate quantities of enzymes and indicators onto the laminates. Dye is dispensed onto the laminate from a dye dispenser 40. A computer 41 is programmed to monitor the amount of reactants and indicators applied to the laminate. A blood filter 42 and an absorbent pad 43 are applied to the laminate, the blood filter being applied so that it is the lower layer. The filter assembly is then sealed by a sealing means 44, and the insert for one device is punched out to the correct size by a punching means 45. Waste film is drawn up by a waste wrap-up 46, and the insert is transferred to the main assembly line.

A typical assay device made by the process of the present invention is shown in in FIG. 3.

A sample well 51 is optionally provided on an assay device according to the present invention 50. This sample well includes a well for receiving a sample, and means from which the sample is transferred to the remaining parts of the measuring device 52. The well is designed such that the analytical process will not be triggered until a certain minimum amount of sample has been deposited in the well. This minimum amount of sample must be sufficient to fill the entire metering or measuring area device, thus avoiding interruption of the analytical process on one side, and insuring that there are no inaccurate results which might result from insufficient amounts of sample deposited on the device.

The sample well is located on the test device such that the sample well is positioned at a lower level than the first location to which the sample must be applied, hereinafter referred to as the initiation area 53. The sample well is connected to the initiation area by means of a siphon means 52 which is created by a channel between one of the ascending surfaces of the sample well and a flat tab protruding into the well. Surprisingly, this configuration functions as a siphon although the sides of the tab are not attached directly to the well. When the liquid sample is of a sufficient volume to conduct an accurate measurement, the fluid sample flows into the siphon and into the initiation area of the measurement device. Sample thus is not drawn from the sample well unless there is sufficient sample to conduct a measurement. The initiation area of the measurement device may be any area on the measurement device that can be used to hold a sample prior to testing. The initiation area may consist of an absorbent material such as glass fiber paper or loosely woven fabric, a capillary network, or some other construction such that, when the sample contacts the initiation area, the sample is drawn to this area. Thus, in one embodiment of a device produced according to the present invention, the device is designed to ensure that only a sample above a minimum volume is drawn into a test device.

In one embodiment of a device made according to the present invention, the fluid sample measuring device comprises three distinct parts:

1. A sample well 51 into which sample is introduced so as to meter the sample to ensure that sufficient sample is present to conduct an assay;

2. A first reservoir or assay initiation area 53 located at a level above the sample well; and 3. Means for connecting the sample well and the initiation area by which liquid can readily flow, resulting in a siphoning action from the sample well to the assay initiation area 52.

To ensure that sufficient sample is applied to the test device to provide an accurate reading, the sample well is located in front of the assay initiation area, and the sample well and the sample initiation area are connected by a structure that functions like a siphon so that sample can be drawn through the siphon means from the sample well into the first reservoir.

The assay initiation area can be of any construction which can contain a fluid sample, such as a porous pad or an open well, or any matrix, so long as the second reservoir has enough pulling force to draw the sample from the sample well. In one embodiment of the present invention, the sample well comprises an open well into which the user drops a few drops of fluid sample, such as blood from a finger stick.

The assay initiation area must be made such that it draws liquid from the first reservoir through the siphon means when the sample contacts the second reservoir.

The siphon means must be constructed such that it exhibits little or no capillary activity, so that the level of liquid in the siphon means is approximately the same as in the sample well.

The sample initiation area is connected to a reservoir 54 by a detection zone 55. This detection zone includes a chromatographic indicator system to display quantitatively the amount of analyte in the sample. There is at least one chromatic chemical indicator immobilized in the detection zone in a calibrated or predetermined concentration. In the detection zone, the fluid sample interacts with the chromatic chemical indicator. The chromatic chemical indicator detects the analyte in the fluid sample by reacting with the analyte, a reaction product of the analyte, or a labelled analogue, developing a color. The colored portion of the detection zone caused by reaction of the chromatic chemical indicator with the analyte, or a derivative thereof, as observed after the capillary action is terminated, corresponds to the concentration of the analyte in the fluid sample. A scale is provided along the length of the detection zone channel to readily equate the colored portion of the channel to the concentration of analyte.

To quantify an analyte using a device of this invention, a fluid sample is deposited into the sample well. If there is sufficient volume of sample to conduct an assay, the sample is drawn up into the assay initiation area through the siphon means. There may be a separation zone below the assay initiation area to remove any solids suspended in the fluid sample. The fluid sample is then drawn through the detection zone by capillary and/or wicking action to the reservoir. The reservoir contains an absorbent. The reservoir draws the fluid sample through the detection zone and, when the reservoir is filled with the fluid sample, the capillary and/or wicking action is terminated. While the fluid sample is being drawn through the detection zone, the chromatographic indicator is permeated with the fluid sample. The detection zone includes a suitable indicator immobilized therein in a predetermined concentration to react with the analyte. Thus, the analyte in the fluid sample is completely reacted in a single step or a series of chemical reactions with the chromatic chemical indicator.

In another embodiment of the present invention, the assay initiation area comprises an absorbent pad, with a plastic tab extending into the sample well to create a siphon tube.

In order to prevent the development of a rocket-shaped curve to the colored detection column, the flow of the liquid through the detection zone can be forced through a tortuous path. This tortuous path can be effected by providing a roughened or knurled surface at the bottom of the detection zone, or by introducing a mesh-like fabric into the detection zone to break up the flow of the fluid through the detection zone.

The indicator can be immobilized in the detection zone in a variety of ways. For example, a membrane can be provided onto which the indicator is immobilized, or the indicator can coat the fibers of the mesh used to break up the path of the fluid flowing through the detection zone. Thus, the flow through the detection zone as well as the path to and through the indicator can be controlled by varying the configuration and materials of the detector.

The measurement channel contains or encloses at least one reagent for detecting the presence of a selected analyte in the sample. The reagent used can be a combination of compounds and/or enzymes that react simultaneously or sequentially with the selected analyte to produce a detectable reaction product. Desirably, the detectable reaction product produces a color change that is visible to the naked eye.

A great variety of reagents for detecting the presence of an analyte in a fluid sample are known in the art and are commercially available. These reagents must be immobilized in some fashion either on the wall of the channel or in a material that is, desirably, stationary within the channel. When more than one reagent is required to detect an analyte, the reagents are, desirably, immobilized in their reaction sequence within the channel or within the first open reservoir and the channel.

The reagent that produces the detectable or chromatic reaction product must be present in a calibrated or predetermined concentration within the channel. The term "chromatic chemical indicator" is used in this sense to include the reagent or combination of reagents necessary to detect a selected analyte in a fluid sample, including a chromatic chemical indicator to produce visible results. The term "predetermined concentration" is used herein to include a concentration of one or more chromatic chemical indicators and/or other reagents that is necessary, in accordance with the present invention, to produce the reaction results desired for a particular test.

One embodiment of the present invention has a material that is stationary within the channel. This material is preferably a natural or synthetic membrane. Suitable membranes for use in this invention are capable of receiving and immobilizing the selected chromatic chemical indicator and are chemically compatible with the selected chromatic chemical indicator. Suitable membranes are commercially available and can be porous or fibrous materials including filter paper or nylon cloth. The membrane is desirably an integral part of the channel, such as the bottom of the channel, and is sealed in place.

Another embodiment of the invention has at least two zones on the membrane within the channel. An initial reaction zone provides reagents to mix and react with an analyte without formation of color to form an intermediate compound. A chromatic reaction zone provides reagents to mix and react with the intermediate compound to cause color formation. Many combinations of multiple zone reactions, with or without the formation of intermediate compounds, can be provided with the present invention.

The device includes means for metering the volume of fluid sample that passes through the channel. This means for metering is, desirably, a "pull" compartment or a reservoir filled with an absorbent. The geometry, physical nature, and method of incorporation of this pull compartment and the channel can be configured to meter precisely the volume and rate of flow of the biological material through the channel. The pull compartment can contain absorbent or porous materials such as filter paper or porous plastic materials to control further the volume and/or rate of flow of the biological material through the channel.

The means for metering the flow of fluid sample through the channel can include a variety of geometric configurations and/or combinations of materials. The void volume of the reservoir is the most critical parameter of the means for metering the flow of sample. The density and composition of the material or membrane in the channel as well as the density and composition of any material which is optionally present in the reservoir can be another parameter effecting the means for altering the flow of the sample. For example, the hydrophilic character of materials in the channel or of a thermoformed moisture barrier used to manufacture the upper surface of the channel significantly affect the flow of a fluid sample through the device. The reservoir, in the preferred embodiment of the invention, contains an absorbent of precise volume and precise solid volume. The reservoir draws a precisely metered amount of liquid through the channel. The reservoir thus provides a self-metering feature for the device.

Regardless of the materials or geometric configuration chosen, it is critical that effective and complete interaction of the analyte in the fluid sample or a derivative thereof occur with the chromatic chemical indicator. The means for metering the flow of a fluid sample in this invention provides a quantitative assay result in at least ten minutes, and, preferably, in at least three minutes.

The dimensions of the device according to the present invention can vary with the intended use. Factors that can vary the dimensions of the device include the amount or nature of the chromatic chemical indicator necessary to perform the desired test for a concentration of analyte in a fluid sample to be tested. The dimensions of the device can be selected to control the reaction time of analyte and chromatic chemical indicator and to control the time required to complete the test. Generally, the device is about 70 to 200 millimeters long, about 20 to about 30 millimeters wide, and about 3 to about 15 millimeters high. The opening, through which the sample is placed into the sample well, is desirably between about 3 millimeters and about 15 millimeters. The initiation area is preferably between about 6 millimeters and 35 millimeters in total length, including the opening to the initiation area, and between about 8 millimeters and about 15 millimeters in width. The channel is desirably a length sufficient to permit the analyte and chromatic chemical indicator to interact and perform the desired analytical test. The dimensions are desirably sufficient to permit capillary action of the fluid sample. A channel that permits capillary action to occur is desirably between about 50 millimeters and 150 millimeters in length and between about 2 millimeter and 6 millimeters in width. The reservoir is between about 10 millimeter and about 30 millimeters in length and about the same width as the initiation area.

A great variety of materials can be used for manufacturing an assay device according to the present invention. The membrane used in the device may be an "activated" membrane. Activated membranes have reactive chemical groups which react with amino and carboxyl groups of proteins, antibodies and dyes in order to form covalent bonds. Commercial sources for suitable membrane materials include Immobilon-AV Affinity Membranes, from Millipore Intertech, Bedford, Mass. 01730. These membranes consist of chemically derivatized hydrophilic polyvinylidene fluoride. Alternative membranes are Immunodyne Membranes, from Pall Biosupport Corporation, Subsidiary of Pall Corporation, Glen Cove, N.Y., 11542. These membranes consist of chemically modified Nylon 6.

The top cover of the device consists of clear 0.010 inch thick PVC roll stock. The bottom base may be made of the same material, or can be manufactured from SARAN reinforced PVC or a polyethylene laminate. A removable peel-off protective strip, covering the upper surface of the device, is desirably provided, and consists of polyethylene-laminated aluminum foil.

The measurement scale portion of the device requires a dye to be immobilized on a porous solid support which is contiguous with a mostly open channel through which a sample such as plasma flows. The dye should be firmly immobilized so that the dye can change color in the presence of hydrogen peroxide or an intermediate species, for example, but not move with the flow of sample through the measurement zone channel. Various methods of immobilizing the dye on a porous matrix such as bibulous filter paper were found to be unsatisfactory. Firstly, the paper absorbs and retains an undesirably large portion of the sample flowing in the channel under the paper. This property is most undesirable in a test where the sample is obtained from drops of blood from a finger stick and the separated plasma is the only fluid used in the device. From two drops of blood, only approximately 30 to 40 microliters of plasma are obtained after separation of red blood cells. Therefore, the fluid sample is in very limited supply. The second disadvantage of immobilizing the dye on a bibulous material is that it is difficult to achieve the desired uniformity of dye distribution, which leads to imprecise measurements. Another disadvantage of using dye immobilized to a bibulous support is that the dye color reaction is slowed because the hydrogen peroxide must diffuse from the open channel to the site of unreacted dye. In practice, this leads to differently color development from the surface of the bibulous support closest to the sample in the channel (more color) to the surface farthest from the channel (less color). These disadvantages precluded the use of previously described methods for immobilizing dye on a porous matrix for use in the device produced according to the present invention.

By immobilizing the dye on small particles, i.e., particles preferably less than 30 microns in diameter, and mixing the dye particles with a film former in an appropriate solvent, and applying the resulting suspension onto a woven monofilament cloth in a very fine coating, the problems of immobilizing the dye on a support were overcome. The thin, porous dye particle containing film exhibited minimal fluid absorption, excellent dye distribution, and far less differential color development from the top to the bottom of the immobilized dye layer film.

Although the dye layer film is still very porous, as evidenced by the rapid color development when exposed to hydrogen peroxide, the amount of fluid absorbed and retained is far less than that observed with bibulous material. This is because the thin coating is applied onto a monofilament fabric, as opposed to a multifilamentary bibulous material with a large number of capillary passages which imbibe fluid.

It is important to the proper function of the device that the dye layer fabric be placed substantially immediately adjacent to a mostly open channel through which the sample could flow, and from which hydrogen peroxide can diffuse into the dye layer. The construction of this mostly open channel under the dye layer can be formed by hot stamping an impression of the channel into a thermoformable material such as polypropylene. The channel can also be formed by injection molding the part from a material such as polystyrene.

The dye layer fabric was impulse heat sealed to polypropylene film, bonding it to the polypropylene. As expected, the impulse heat seal formed a boundary which contained the liquid sample within the channel. Since the flow down the channel was too slow to make the device practical for use, a second layer of fabric, which had been treated to render it hydrophilic, was placed between the dye layer fabric and the polypropylene, and then impulse heat sealed. The second layer of fabric introduced a mostly open channel under the dye layer fabric while introducing turbulent flow as the sample flowed through the fibers. Unexpectedly, this technique produced very uniform, reproducible volume channels with well defined edges. This was unexpected because ordinarily one would expect that the application of sufficient heat to melt the fibers completely would also partially melt and distort the fibers away from the seal towards the interior of the channel. Microscopic evaluation of the seal showed that the nylon fibers of both the dye layer and the channel layer were intact and not melted in the seal area, and the polypropylene on the bottom had melted and extruded into the fibers of both layers, effectively forming a seal.

This sealing technique was also conducted with polyester monofilament filter cloth for both the dye layer and the channel layer, which was sealed to a polyethylene film. Again, a very good seal was formed which effectively constructed the channel, and the precise dimensions of the channel layer fabric formed the height of the channel while the distance between the parallel seal lines formed the width. Once again, microscopic evaluation showed that the polyethylene had melted and extruded into the fabric, thereby forming the seal.

The sealing technique of the present invention works well with any combination of material in which the fabric has an open mesh and a melting point higher than the material to which the fabric is being sealed.

The measurement zone which consists of the dye layer fabric 307, channel layer fabric 308, and the sealing film 311 are impulse heat sealed to form a channel and inserted as a unit into a support tray 309. The channel layer fabric and sealing film extend beyond the end of the measurement channel by about one centimeter. On the extension nearest the sample well are placed a pad 305 impregnated with appropriate enzymes and other commercial reaction components, filtration pads 304 which separate red blood cells from plasma, and an absorbent pad 303 which first draws the fluid from the sample well.

The absorbent pad which draws the fluid from the sample well is typically a non-woven low density fabric such as polyolefin or polyester which has a sufficient absorbency to draw the fluid from the sample well but is not so absorbant as to prevent flow of the fluid into the contiguous filtration pads. In the case of a whole blood sample, the first absorbent pad can also be impregnated with an anticoagulant such as EDTA or heparin, so that the anticoagulant is dissolved and thoroughly mixed with the sample as the blood is absorbed. The first absorbent pad can also be used as a means to introduce other additives to pre-treat the sample before the fluid moves to other sections of the device.

At the opposite end of the measurement zone, the draw zone material 306 is placed on top of the channel layer fabric in such a manner that fluid exiting the channel is absorbed by the draw zone material. The draw zone material can be paper, fiberglass, or synthetic porous material or any other type of material which is capable of absorbing a defined quantity of fluid.

The second component of a two part dye system is applied to the dye layer fabric in a controlled manner, preferably using an ink jet printer or by using an ultrasonic spray nozzle to limit overspray. This second dye component is applied such that the concentration of the second dye forms a gradient from the beginning to the end of the channel. This gradient is used to render non-linear color bar development linear by applying more of the second dye at the beginning of the channel than at the end, i.e., a gradient of decreasing concentration of the dye. The application of the second dye can also be controlled to tailor the color bar response to the desired measurement scale of the analyte.

A clear cover 301 is placed over the measurement zone channel in such a way that a measurement scale is printed immediately over the channel. The printer is controlled by a computer, which is in turn a component in a feedback control loop on the manufacturing machine. Samples of the product are randomly and continuously taken during the production run, and a standard solution with a known quantity of analyte is applied to these samples. The resulting length of the color bar is measured, and the results are fed into the computer database which continuously performs a trend analysis on the data to determine whether the bar is getting progressively longer or shorter. The software then automatically expands or contracts the measurement scale to ensure the accuracy of the test.

FIG. 3 shows an exploded view of the assembled device 310 prepared according to the present invention in which each of the components of one embodiment of the device is shown individually. The device rests upon a base support 309, on which is placed a channel layer 308 which contains a dye layer or other indicator layer. The draw zone 306 aids in moving the fluid sample from the initiation area through the measurement channel 308, which is shown assembled as 320. The sample is introduced to the device through an absorbent pad 303, which forms the assay initiation area. A blood filter 304 may be provided to filter unsanted solids from a sample of whole blood. The sample then contacts an enzyme zone 305 to begin the indication part of the assay. A top cover 301 protects the device from contamination during storage.

The process of the present invention is particularly well suited to use on an automated assembly machine which conducts sequential, controlled assembly of the device. Critical stations, such as the printer for the measurement scale, are feedback controlled by (conventional) computer software based upon real time input from on and off line quality control data.

EXAMPLE 1 Preparation of Dyed Films

Preparation of Cellulose

In a 100 mL graduated cylinder were combined 2 grams dyed MCC105 (PQ-SH-MCC105 N10) 20 micrometer microcrystalline cellulose, and 2 grams virgin MCC06 (6 micron undyed microcrystalline cellulose). To the solids was added sufficient 0.1M $NaH_2PO_4$ solution to make up a total volume of 30 mL.

The graduated cylinder was placed into a 600 mL beaker filled with approximately 300 mL of iced tap water to act as a cooling jacket.

The end of an 18G S25N probe for a Tekmar Tissumizer was then lowered into the solution into the graduate to as great a depth as is permitted by the Tissumizer housing. Power was applied using a Tekmar TR-10 power controller at 75% of full scale for 20 minutes.

Upon completion of the homogenization of the cellulose, the tissumizer was turned off and raised out of the graduate. Solution remaining on the probe is rinsed into the graduate using additional 0.1 M $NaH_2PO_4$.

The suspension was then transferred to 15 mL Corex centrifuge tubes. Additional 0.1 M $NaH_2PO_4$ solution was used to rinse the graduate of cellulose. The centrifuge tubes were placed into a HERAEUS model 3632 Medifuge and centrifuged at 3500 rpm for two minutes.

After centrifuging, the supernatant liquid was drawn off and discarded. The solids were removed form the centrifuge tube using a spatula, and placed into a preweighed 100 mL beaker.

Preparation of the Casting Solution

The weight of cellulose slurry in the beaker was determined by difference weighing. Into a 25 mL beaker was weighed 4 grams of washed (acetone and water), undyed polyvinyl alcohol (PVOH) and 6 grams 0.1M $NaH_2PO_4$. The beaker was heated gently until a clear, viscous solution was obtained. The amount of polyvinyl alcohol solution to be added to the casting solution was calculated using the equation:

$$(\text{grams cellulose slurry} - 3.0)0.429 = \text{grams } 40\% \text{ PVOH}$$

The appropriate amount of 40% PVOH solution was added to the beaker containing the cellulose slurry.

Using a solution of 3-methyl-2-benzothiazolinone hydrazone hydrochloride hydrate (MBTH) in distilled, deionized water at a concentration of 40 mg MBTH/mL, an appropriate amount of MBTH was added to the casting paste by piperting. Typically, 15 mg MBTH (0.375 mL solution) was used. The components were thoroughly mixed.

In a dry environment, 9 mg ±0.5 of horseradish peroxidase (POD) enzyme was weighed into a weighing pan. The enzyme was dissolved in a minimum amount of water (about 1 mL) and added to the casting solution. A rinse of the weight pan using about 1 mL of water was also added to the mixture. Again, the components were thoroughly mixed.

A test of the solution for proper composition was made by placing a small amount of the paste onto a slide and developing it with a few drops of 20 mM $H_2O_2$. A color change should result.

Preparation of the Support Film

On a section of clean glass, a swatch of pre-shrunk, heat set polyethylene terephthalate (PET) fabric having a nominal opening size of 105 microns was secured. This securing was best accomplished by placing double sided tape onto the glass at the edges of the cloth, exposing the adhesive at one edge, sealing the cloth to the adhesive, then exposing the second adhesive strip and stretching the fabric as it was sealed to the second strip. Finally, all four edges of the fabric were sealed with single sided tape.

The fabric may be corona treated before attaching it to the plate. However, if this is done, a minimum of two hours should be allowed between treatment and film casting.

Casting the Film

After preparation of the casting paste and fabric, the paste was laid onto the top of the fabric in a thick line by pouring or scraping the paste from the beaker. When the paste was completely in place, a casting knife was drawn down the fabric length in a single, smooth motion leaving behind a smooth even layer of the casting film. The entire plate was then transferred to a dry atmosphere and allowed to evaporate to dryness. Typically, the material can be used for testing in about three hours.

A mixture of the following was cast onto heat set PET fabric having a nominal mesh size of 105 microns using a Gardner casting knife set at 1 mil:
3.9 g PQ-Stt-MCC006 (N17) slurry in MeOH
1.5 g 40% PVAc in MeOH
1.0 mL 40 mg/mL fb-MBTH/MeOH
0.0096 g POD in 0.5 mL H20/1.0 mL MeOH The resulting film had a light yellow color from the dyed cellulose.

It should be noted that methanol can be used in preference to the 0.1 M $NaH_2PO_4$ solution, both in the preparation of the cellulose and in the preparation of the casting solution. The solution of either MBTH or its free base in methanol was preferentially used, usually 40 mg MBTH total. The peroxidase is preferentially dissolved into water and methanol is then added to this solution.

A casting solution was prepared from the following:
3.7 g PQ-Stt-MCCO06 (N17)
1.3 g 40% PVA in methanol
1.0 mL 40 mg/mL MBTH in methanol
0.0088 g POD in 0.5 mL $H_2O$/1.0 mL methanol When the film was removed, no residue remained on the glass. The film was then transferred to a glass sheet for ease of handling. Film flexibility and film-to-fabric adhesion was both excellent with the film showing no tendency to chip, crack or peel with normal handling.

Microscopic examination of the film showed the expected morphology, with the fabric mesh clearly visible on the upper surface. The lower fabric surface was almost completely covered with a layer of coating. The film had a light yellow color from the dyed cellulose. Treatment of sections cut from the film with aqueous 20 mM $H_2O_2$ gave a dark red color.

Devices fabricated with this film showed good characteristics as an indicator strip.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

What is claimed is:

1. In a method for making a multilayer assaying device for fluid samples by assembling layers and sealing said layers together, said layers comprising elements corresponding to an assay initiation area and elements corresponding to a measurement zone to form an assaying device comprising a sample initiation area and a measurement zone, whereby a fluid sample to be assayed flows from the sample initiation zone through the measurement zone, the improvement comprising said measurement zone being produced by heat sealing a support material to a woven mesh material to form a seal along the sides of said measurement zone, wherein the material forming the support melts during heat sealing while the material forming the woven mesh does not melt during heat sealing whereby the melting points of the woven mesh material and the support material are chosen so that during heat sealing the material forming the support flows into the woven mesh, and that the amount of heat applied to the measurement zone determines how much support material flows into the mesh to define the volume of the measurement zone.

2. The method according to claim 1 wherein said support material is polyethylene and said woven mesh material is polyester.

3. The method according to claim 1 wherein said measurement zone is made by heat sealing together dye layer fabric, channel layer fabric and sealing film, and said measurement zone is inserted into a support tray.

4. The method according to claim 1 wherein said support material is polyethylene and said woven mesh material is nylon.

5. The method of claim 1, wherein said multilayer assaying device further comprises layers comprising elements corresponding to a draw zone.

6. In a method for making a multilayer assaying device for fluid samples by assembling layers and sealing said layers together, said layers comprising elements corresponding to an assay initiation area and elements corresponding to a measurement zone, to form an assaying device comprising an assay in initiation area and a measurement zone whereby a fluid sample to be assayed flows from the assay initiation area through the measurement zone, the improvement comprising said measurement zone being produced prior to assembling said layers by heat sealing a support material to a woven mesh material to form a seal along the sides of said measurement zone, wherein the material forming the support melts during heat sealing whereby the melting points of the woven mesh material and the support material are chosen so that during heat sealing the material forming the support flows into the woven mesh and the amount of heat applied to the measurement zone determines how much support material flows into the mesh to define the volume of the measurement zone and applying a two-part dye system along the length of the measurement zone;
   said dye system applied by immobilizing a second dye component on particles;
   suspending said particles in a binder;
   mixing said binder and particles with a first dye component to form a dye mixture;
   applying said dye mixture to the woven mesh material in said measurement zone.

7. The method according to claim 6 wherein said dye mixture is applied with an ink jet printer.

8. The method according to claim 6 wherein on an assembly line for making assaying devices according to claim 6, representative assaying devices are continuously sampled and tested by applying a standard solution with a known quantity of analyte to said assay devices wherein color bars are formed by said analyte, the lengths of color bars in said devices are continuously compiled and subjected to trend analysis, and the distance between divisions of a measurement scale on said measurement zone are automatically adjusted by a computer which controls an ink jet printer.

9. The method according to claim 6 wherein said particles are selected from the group consisting of microcrystalline cellulose, silica and latex.

10. The method according to claim 6 wherein said binder is selected from the group consisting of polyvinyl alcohol, polyvinyl acetate, and cellulose acetate.

* * * * *